United States Patent
Müller et al.

[11] Patent Number: 5,360,426
[45] Date of Patent: Nov. 1, 1994

[54] FORCE-CONTROLLED CONTACT APPLICATOR FOR LASER RADIATION

[75] Inventors: Gerhard Müller; Norbert Müller-Stolzenburg, both of Berlin, Germany

[73] Assignee: Carl-Zeiss-Stiftung, Heidenheim, Germany

[21] Appl. No.: 776,562

[22] Filed: Oct. 15, 1991

[30] Foreign Application Priority Data

Oct. 12, 1990 [DE] Germany .............................. 4032860

[51] Int. Cl.$^5$ .............................................. A61N 5/06
[52] U.S. Cl. ......................................... 606/13; 606/3; 606/10; 607/88; 607/89
[58] Field of Search ...................... 606/2–19; 128/395, 397, 398; 607/88–90

[56] References Cited

U.S. PATENT DOCUMENTS

| | | | |
|---|---|---|---|
| 3,242,314 | 3/1966 | Eckles . | |
| 3,622,743 | 11/1971 | Muncheryan | 606/2 |
| 4,273,127 | 6/1981 | Auth et al. | 606/3 |
| 4,573,466 | 3/1986 | Simada | 606/11 |
| 4,756,597 | 7/1988 | Hahn et al. | 606/15 |
| 4,837,857 | 6/1989 | Scheller et al. | 606/4 |
| 4,906,812 | 3/1990 | Nied et al. . | |

FOREIGN PATENT DOCUMENTS

| | | | |
|---|---|---|---|
| 0307544 | 3/1989 | European Pat. Off. . | |
| 3729288 | 3/1989 | Germany | 606/3 |
| 3911853 | 10/1990 | Germany . | |
| 58-224091 | 12/1983 | Japan . | |

*Primary Examiner*—David M. Shay
*Attorney, Agent, or Firm*—Walter Ottesen

[57] ABSTRACT

A contact applicator arrangement for applying laser radiation to an object is disclosed. The contact applicator arrangement includes: a holder having an outer surface and defining a longitudinal axis; the holder having an outlet formed in the outer surface for passing the radiation from the holder to the object; a radiation guide mounted in the holder for guiding the radiation through the outlet; and, an element displaceably mounted in the holder so as to be movable along the longitudinal axis in response to a contact pressure applied on the element. The element is movable to a first position wherein the element extends outwardly beyond the surface of the holder and to a second position rearward of the first position. These first and second positions define a displacement range of the element. A spring resiliently biases the element in opposition to the contact pressure to define a pregiven force within the displacement range of the element. A laser radiation supply supplies radiation to the radiation guide and a switching circuit switches the radiation supply on when the element is moved back to the first position and remains on within the displacement range and switches the radiation supply off when the element reaches the second position and leaves the displacement range.

16 Claims, 2 Drawing Sheets

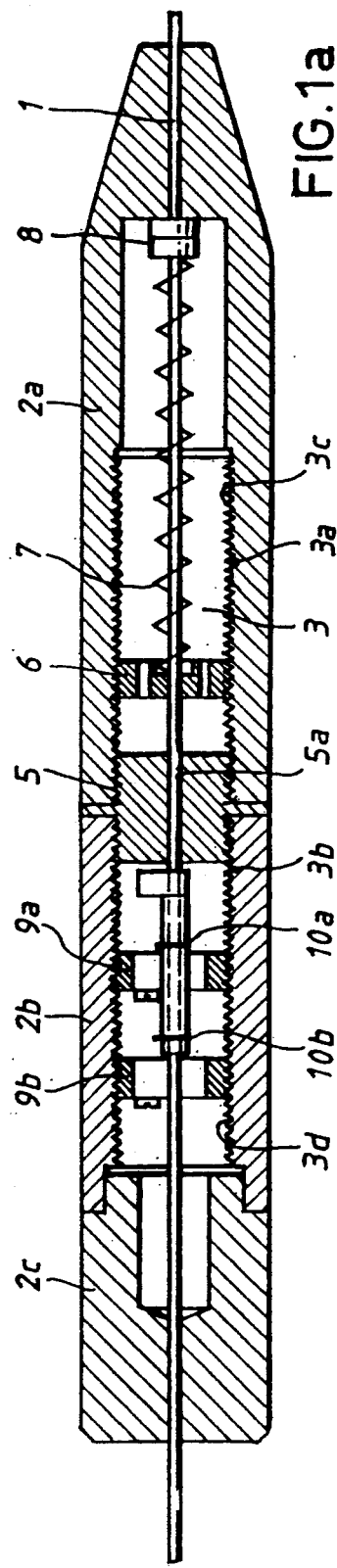
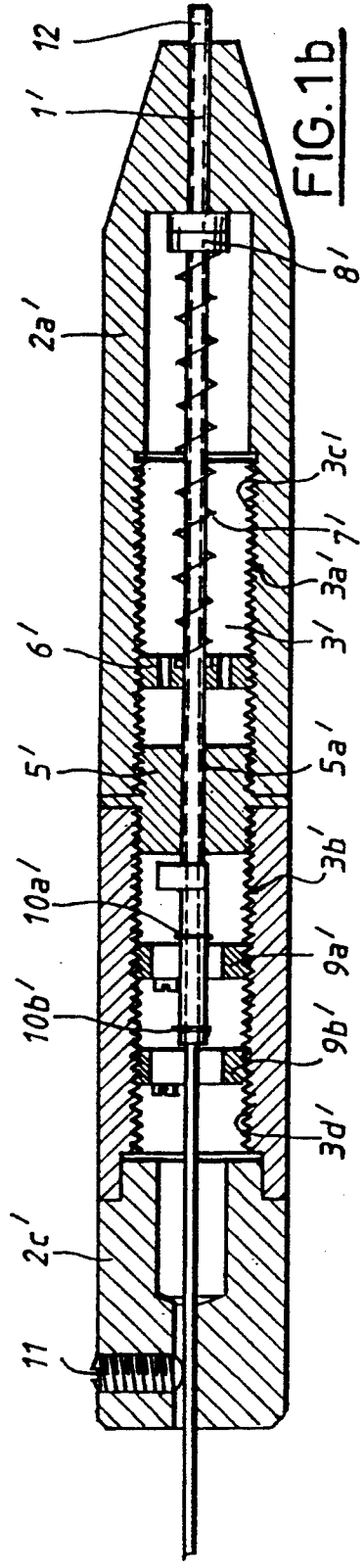
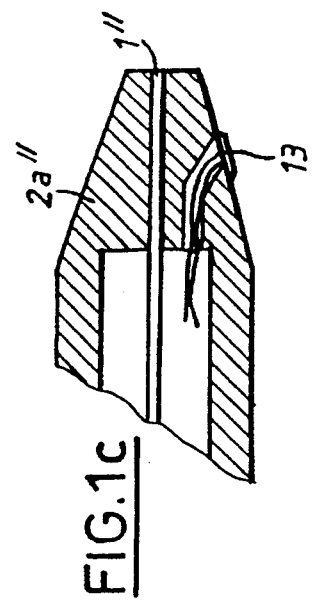

5,360,426

FORCE-CONTROLLED CONTACT APPLICATOR FOR LASER RADIATION

BACKGROUND OF THE INVENTION

It is known to transmit laser radiation in the range between 250 nm and 11 μm via optical light-wave conductors such as wave guides and to process materials therewith in the widest sense. These applications also extend into the area of medicine.

It is likewise known that the effective portion of the applied laser energy in the actual target volume can be controlled only with great difficulty in heterogeneous materials because of multiple scattering at texture boundaries. For this reason, a work result can be estimated only with difficulty for a given laser energy.

SUMMARY OF THE INVENTION

It is an object of the invention to configure a laser applicator of the kind referred to above so that the laser radiation can be applied with controlled parameters even without the need for operating additional adjusting devices or ancillary apparatus.

In various applications in industry and medicine, there is a need for providing laser radiation under prespecified force conditions and to ensure that the laser radiation is triggered only after a pregiven contact force of the optical light wave conductor on the material to be processed is reached. The invention herein is based upon the foregoing.

Often, the laser radiation must be effective over a prespecified time duration. This is the case in the most various applications in microelectronics and micromaterial processing such as in the mechanical working of composite materials.

Two approaches are generally available with regard to the foregoing. In the first approach, an element is provided which lies in contact engagement with the surface of the material during the laser radiation. This element is driven through a stroke range by a source for a force as constant as possible with this element being preferably resiliently journalled. A second approach is to provide a measuring device for the contact force which notifies the operator that the applied contact force is within a pregiven range. This notification to the operator can be via an acoustic signal or by a switch-on of the laser source.

The above two approaches can be combined with each other so that the measuring element for the contact pressure pursuant to the second approach defines a resiliently journalled element and not a force sensor which is essentially rigidly held.

The solution provided by the invention is especially advantageous for use in medicine where outer tissue layers must first be brought into intimate contact mechanically with deeper tissue layers before a coagulation necrosis for joining the tissue layers can be produced via the triggered laser radiation. This intimate contact between outer and inner tissue layers, for example, reduces scattering and provides a better adherence.

With respect to the invention, it is also advantageous that target structures can be charged with laser energy in a significantly more precise dosage via the controlled introduction of force via the beam guide system of the laser apparatus. The above target structures are especially heterogeneous composite materials as they are present in the application areas of microelectronics and microstructure technology and especially in medicine.

In the application in the area of medicine, it should be considered that radiation guidance systems which have come into use as a rule use an optical light wave guide and, as a consequence thereof, the danger of injury to the tissue structure is present because of the mechanical contact of the tissue surface with a contact force which is too great. On the other hand, it is desired that tissue layers be compressed with a specific maximum possible force to the extent that multiple scattering caused by the cellular texture is reduced to a minimum and therefore the full transmitted laser energy is available at the target location.

In order to ensure, on the one hand that the introduction of the laser radiation takes place optimally while, on the other hand, the operator is advised of a dangerous condition when the permissible contact pressure is exceeded, two switch points are provided according to another embodiment of the invention. With an increase in the applied contact pressure, the laser is switched on at the first switching point and again switched off at the second switching point. In this way, the preferred or necessary work conditions are maintained without requiring special additional attention of the operator and there are no other elements to be actuated so that the operator's complete concentration can be devoted exclusively to the work area all the time.

The pressure on the work surface is sensed by a sensing element attached to the holder with the sensing element preferably responding to pressure forces acting in the direction of the fiber. The sensing element is preferably journalled so as to be resiliently displaceable relative to the holder. The sensing element can be formed by the fiber end as well as by a tube surrounding the fiber. In the first-mentioned case, the end is mechanically held and displaceably journalled in an outer mechanical tube pushed over the fiber.

For the controlled introduction of force, either a spring is connected to the mechanical holder of the fiber or is mechanically connected to the sleeve and, pursuant to the solution adopted, the fiber projecting out of the sleeve is pushed back against the spring force against a preadjustable stop in the sleeve until the desired force is applied to the tissue via a preadjustable stop. On the other hand, the tube is pushed back with respect to the fixed fiber with the tube projecting with reference to the fiber end until likewise the desired force is applied to the tissue as before by a preadjustable stop.

In another preferred embodiment, an electrical contact is actuated via the preadjustable stop of the spring displacement path with the contact then triggering the laser radiation.

In another embodiment of the invention, two contacts are provided on the mechanically extended spring path which then define an upper and lower limit value via the spring path for the mechanical force to be developed for compressing the target structure with the upper limit value being used to switch off the laser and to trigger an alarm signal.

In a preferred embodiment for performing a cyclocoagulation in the eye, a fiber rounded hemispherically at its distal end is provided with a mechanically fixed sleeve having a stop. Preferably, this sleeve is made of metal and has a folded over ring and can be connected in the inner guidance piece of the holder via a quick screw with the spring connection. In the holder itself, the electrical contacts of the limit value indicators of the spring displacement path are connected in series with a triggering foot switch with the control of the laser apparatus. The limit value indicator device can be adjusted with respect to the desired contact pressure.

Mechanical force-controlled elements on radiation guiding hollow conductors or multi-mirror articulated arms are likewise suitable for application with the invention.

The driven force-controlled applicator includes a mechanical return force because of the configuration of the spring path. It can be disturbing in various applications and especially in the case of desirable perforations of tissue layers. The action of a specific force on the applicator can cause the applicator to be shortened by a specified amount and, on the other hand, causes the tissue to be mechanically deformed. This problem, in the case of a targeted and desired perforation, can lead to the condition that a sudden failure of the counterforce of the tissue causes the pressure applying fiber to advance too rapidly. In order to prevent this, and according to a further embodiment of the invention, a relatively stiff membrane-like or leaf spring-like holder of the particular movable part of the force applicator can be used in lieu of the spiral spring mentioned initially. The elastic displacements of the membrane-like or leaf spring-like holder can amount to even less than a tenth of a millimeter and can be measured via a wire strain gauge. The electrical signal of the wire strain gauge is then supplied to an evaluation electronic unit by means of which switch-on and switch-off limit values for the laser can be adjustable in proportion to force.

By detecting the applied force via wire strain gauges, a very precise and sensitive possibility exists to use the tolerance range for the force transmission simultaneously as a triggering criteria for the laser radiation and, in this way, to use very precisely radiation and contact with an exact pregiven force introduction. With this embodiment of the invention, of switch-on and switch-off criteria of the laser radiation, further possibilities of application of the basic inventive concept of the force-controlled laser applicator are provided. The switch-on and switch-off criteria are adjustable via wire strain gauges or corresponding pressure gauges or capacitive or inductive displacement sensors.

It is also especially possible to push forward a laser catheter in the angioplasty with controlled force introduction. Laser radiation guiding optical lasers are intended not only for boring or coagulation, but can be used also for cutting tissue with a controlled application of force. These optical fibers are charged with force in the axial direction while applying the corresponding wire strain gauges for measuring the transverse force.

BRIEF DESCRIPTION OF THE DRAWINGS

The invention will now be described with reference to the drawings wherein:

FIG. 1a is a side elevation view, in section, of a first embodiment of the contact applicator according to the invention;

FIG. 1b is also a side elevation view, in section, of a second embodiment of the contact applicator of the invention;

FIG. 1c is a detail view of a portion of a contact applicator equipped with a pressure sensor according to a third embodiment of the invention;

DESCRIPTION OF THE PREFERRED EMBODIMENTS OF THE INVENTION

Figure 2A:
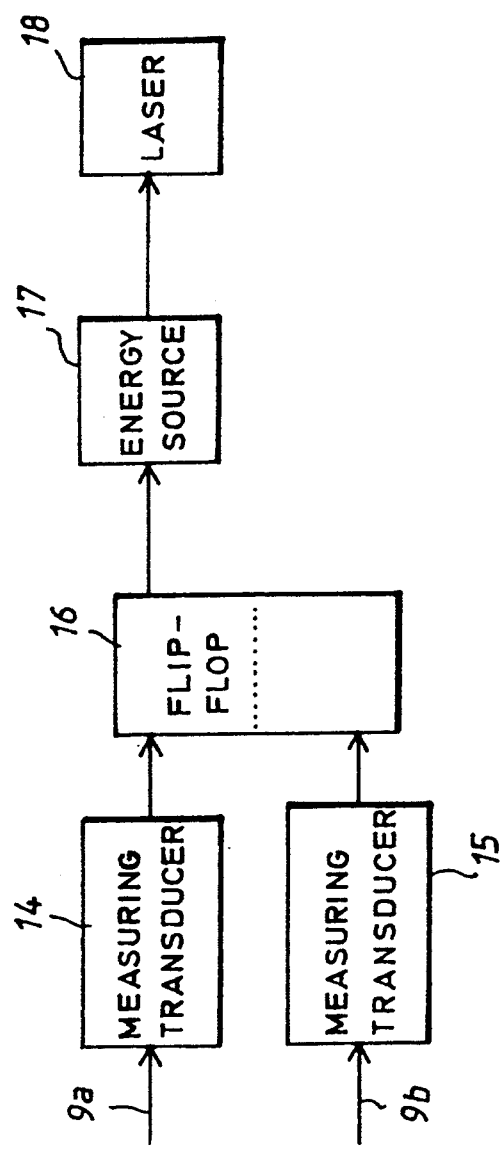
FIG. 2a is a block diagram of the electronic control system for the contact applicator of the invention; and, FIG. 2b is a second embodiment of the control system for the contact applicator of the invention.

In the contact applicator shown in FIG. 1a, a glass fiber conductor 1 is displaceably journalled in a three-part holder comprising segments 2a to 2c. The holder 2a to 2c has approximately the form of a writing instrument with the glass fiber conductor occupying the position of the writing lead. The segments 2a and 2b are provided with a through bore and have respective expanded regions 3a and 3b. The expanded regions 3a and 3b are provided with respective internal threads 3c and 3d, respectively, which extend at least over part of the expanded region. The end segment 2c closes the segment 2b and, in turn, has a pass-through for a glass fiber feedline. The segments 2a and 2b are connected by a threaded coupling piece 5 which, in turn, has a through bore 5a for accommodating the glass fiber conductor 1.

The holder has an overall length of approximately 120 mm with a diameter of 16 mm. The glass fiber conductor 1 projects approximately 3 mm out of the beveled end of segment 2a. An adjustable stop bearing 6 is provided in the internal thread 3c of the recess 3a and is adjustable. A helical spring 7 surrounds the glass fiber conductor 1 in the recess 3a and braces at one end thereof against the stop bearing 6. At its other end, the helical spring 7 lies against the adjusting ring 8 which is fixedly connected to the glass fiber conductor 1 and defines a stop which prevents a further displacement of the glass fiber conductor 1 out of the segment 2a.

When using the holder, a minimum force is required in order to lift the adjusting ring 8 out of its contact position when the tip of the fiber conductor 1 is pressed against the object to be treated. The compression force to be applied changes only slightly because of the length of the helical spring 7 until the fiber conductor is fully pressed inwardly so that it is in a position in which its front face is flush with the front face of the segment 2a of the holder. When the operator senses a resilient resistance, it is ensured that the operator applies a pressure to the tissue to be treated which is within a tolerance range limited by the adopted limit values.

To improve the control capability further, switch means are provided which emit signals in dependence upon the position of the fiber conductor 1 in order to switch on the laser source as soon as the minimum pressure to be applied to the surface is reached and to again switch off the laser source as soon as this pressure is exceeded. These two limit values are identical to the almost completely outwardly displaced position of the light conductor and the almost completely inwardly displaced position. Limit switches 9a and 9b are provided in the segment 2b of the holder which are finely adjustable in their axial position by means of the internal thread 3d provided there. These limit switches 9a and 9b are actuated by activating elements 10a and 10b, respectively, which are connected to the fiber conductor 4. As soon as the element 10a is next to the limit switch 9a because of a displacement of the fiber conductor by a minimal amount, a first signal is emitted which switches on the laser source and triggers a corresponding advisory signal which signals to the operator that the contact pressure is maintained within a pregiven range. The laser is again switched off by a further corresponding signal when the element 10b reaches the limit switch 9b. In this way, the operator can easily maintain the pregiven force limit values.

The embodiment shown in FIG. 1b corresponds in its configuration to that shown in FIG. 1a so that the elements thereof corresponding to those in FIG. 1a are provided with corresponding reference numerals except that a (') is added thereto.

In the embodiment shown in FIG. 1b, the fiber conductor 1' is, however, held in a position with the front face thereof flush with that of the forward segment 2a' of the holder. The fiber conductor passes through a coupling piece 5' and extends through to the end of the holder (segment 2c') and is held in segment 2c' by means of a set screw 11. The coupling piece has a through bore 5a' for accommodating the fiber conductor 1'. A tube 12 is displaceable relative to the fiber conductor for sensing the contact pressure. The tube 12 projects outwardly from the holder approximately 3 mm in the unloaded condition. The tube 12, in turn, is connected to an adjusting ring 8' and to a helical spring 7' with the helical spring being braced on a stop bearing 6'. In the embodiment of FIG. 1b, the tube surrounding the fixed fiber conductor 1' takes over in lieu of the fiber conductor the function of force transmission and activation of the actuating elements 10a' and 10b'. The actuating elements 10a' and 10b' effect a switch-off of the laser source with a displacement of the actuating elements with respect to these switching elements 9a' and 9b'.

A mechanical return announcement for the operator is triggered by the stroke of the light conductor (FIG. 1a) or tube (FIG. 1b). If this return announcement for the operator is not wanted, then in lieu of the switching elements actuated by the movable contacts and in lieu of the helical spring as an element for applying force, pressure sensors can be used which operate with only a slight stroke or without a stroke and emit an electrical signal which switches the laser source on and off within a pregiven contact pressure range. Wire strain gauges, piezo elements and the like can be used as elements of this kind. In lieu of the elements 9 and 10, these elements can be mounted in the holder and emit the corresponding output signal as soon as a corresponding actuating force can be sensed between these elements.

In the embodiment shown in FIG. 1c, a light conductor 1" is fixedly mounted in the forward segment 2a". A pressure sensor 13 which operates with a short stroke or without a stroke is mounted transverse to the direction of the fiber conductor 1". In this way, cutting movements are possible with the holder with the pressure sensor 13 detecting the lateral contact force and switching on and off in a corresponding manner.

In FIG. 2a, an electric control portion is shown which carries out the corresponding switching operations. The output signals of the switch elements 9a and 9b are supplied to measuring transducers 14 and 15, respectively, which, in turn, emit a digital output signal which sets and resets a flip-flop 16. The logic output signal Q of the flip-flop 16 drives the energy source 17 for a laser 18. It is evident that the activation of the laser takes place with the setting and resetting of the flip-flop 16 when the switch-on and switch-off signal is emitted.

Figure 2B:
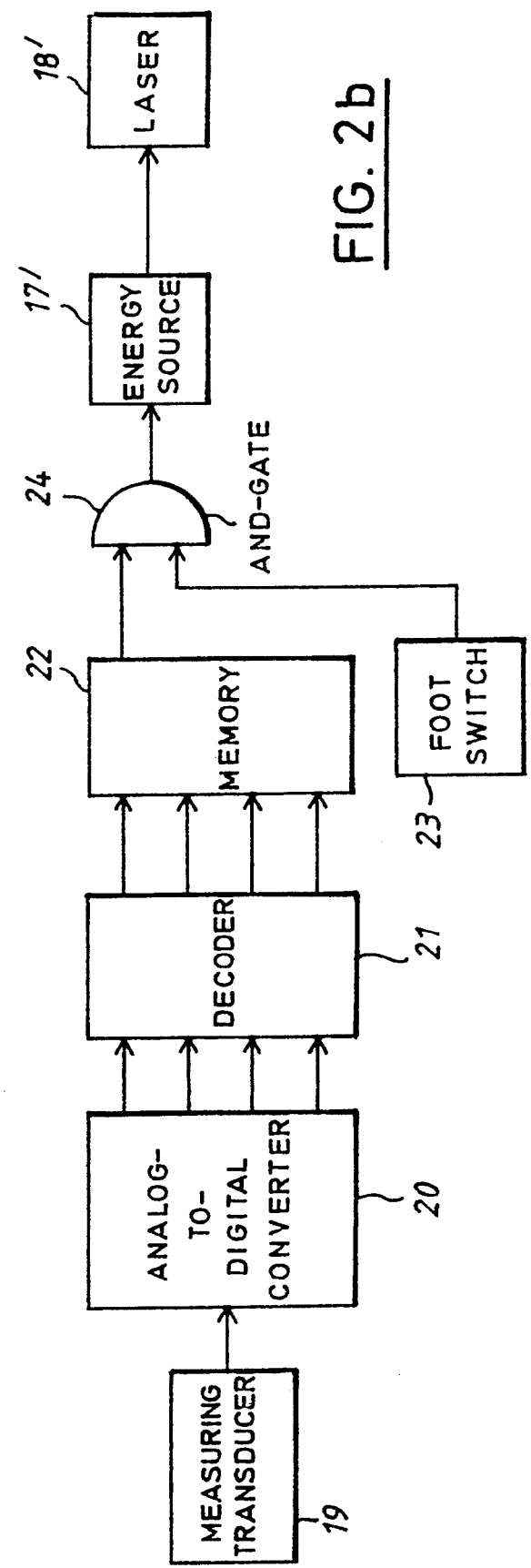

In the block diagram shown in FIG. 2b, a measuring transducer 19 is provided which emits an analog signal proportional to the position of the light conductor 1 or to the tube 12 or to an applied force. This signal is supplied to an analog-to-digital converter 20 which emits, in parallel, digital data via several signal outputs to drive a decoder 21. This decoder 21 evaluates time changes of the input signal so that, for pregiven signal switch-on or switch-off times or when a specific signal level is exceeded for pregiven times, a digital output signal is emitted which output signal is assigned to a time trace of the input signal corresponding thereto. This output signal addresses a preprogrammed switching function in a memory 22 which likewise can be a function of time. In this manner, and with an appropriate programming of the decoder or of the memory, any time-dependent operations of the laser control can be assigned to any desired time-dependent traces of the applied force. Short applied force pulses or pulse sequences or short-term reduction of the force pressure can be controlled up or down in a desired manner or time-dependent preprogrammed intensity traces can be called up. In this way, a one-handed operation is possible wherein the operator can fully concentrate on the area of treatment. As an additional safety element, a foot switch 23 can be provided which together with an AND-gate 24 can influence the output signal of the memory 22 in such a way that the energy source 17' of the laser 18' can only then be activated when the foot switch 23 is also actuated.

It is understood that the foregoing description is that of the preferred embodiments of the invention and that various changes and modifications may be made thereto without departing from the spirit and scope of the invention as defined in the appended claims.

What is claimed is:

1. A contact applicator arrangement for applying laser radiation to an object, the contact applicator arrangement comprising:

a holder having an outer surface and defining a longitudinal axis;

said holder having an outlet formed in said surface for passing the radiation from said holder to the object;

radiation guide means mounted in said holder for guiding the radiation through said outlet;

a pressure sensor mounted on said outer surface of said holder transversely to the direction of said radiation guide means to provide an output signal indicative of contact pressure applied to said sensor when in contact engagement with the object;

laser radiation supply means for supplying radiation to said radiation guide means;

circuit means for switching said radiation supply means on when said output signal reaches a first value and for switching said radiation supply means off when said output signal reaches a second value; and, said holder having a forward end defining said outlet; and, said pressure sensor being mounted virtually at said forward end proximate to said outlet.

2. The contact applicator arrangement of claim 1, said circuit means comprising:

an analog-to-digital converter for receiving said output signal and for emitting a plurality of digital signal outputs;

a decoder for receiving and evaluating said digital signal outputs to provide a decoder output signal; and, a memory containing preprogrammed switching functions and for responding to said decoder output signal in accordance with one of said switching functions to control the output of said laser radiation supply means.

3. The contact applicator arrangement of claim 2, further comprising: an AND-gate having a first input connected to said memory and having a second input and an output; and, an actuator connected to said second input of said AND-gate and being adapted to be activated by an operator of said arrangement; and, said output of said AND-gate being connected to said laser radiation supply means for controlling said laser radiation supply means when an output signal is supplied by said memory and said actuator.

4. The contact applicator arrangement of claim 3, said actuator being a foot switch.

5. A contact applicator arrangement for applying laser radiation to an object, the contact applicator arrangement comprising:

a holder having an outer surface fixed with respect to the applicator arrangement and defining a longitudinal axis;

said holder having an outlet formed in said surface for passing the radiation from said holder to the object;

radiation guide means mounted in said holder for guiding the radiation unfocused through said outlet to the object;

said radiation guide means being displaceably mounted in said holder so as to be movable along said axis in response to a contact pressure applied on said radiation guide means, said radiation guide means being movable to a first position wherein said radiation guide means extends outwardly beyond said surface and to a second position rearward of said first position;

said first and second positions defining a displacement range of said radiation guide means;

resilient biasing means for resiliently biasing said radiation guide means in opposition to said contact pressure to define a pregiven force within said displacement range of said radiation guide means;

laser radiation supply means for supplying radiation to said radiation guide means; and, switching means coacting with said radiation guide means for switching said radiation supply means on when said radiation guide means is moved back to said first position and remaining on within said displacement range and for switching said radiation supply means off when said radiation guide means reaches said second position and leaves said displacement range.

6. The contact applicator arrangement of claim 5, wherein said resilient biasing means applies a predetermined force to said radiation guide means when said radiation guide means reaches said first position.

7. The contact applicator arrangement of claim 5, wherein said switching means includes a first switch mounted in said holder for supplying an output signal when actuated and a first switch actuator mounted on said radiation guide means to close said first switch when said radiation guide means reaches said first position; and, said arrangement further including control means for controlling said radiation supply means to influence said radiation in response to said output signal.

8. The contact applicator arrangement of claim 5, said radiation guide means being a light-wave conductor.

9. The contact applicator arrangement of claim 5, further comprising adjusting means for adjusting the resilient force developed by said resilient biasing means to define a first limit force corresponding to said first position opposing said contact force and a second limit force corresponding to said second position opposing said contact force.

10. The contact applicator arrangement of claim 5, said radiation guide means being a fiber; and, said fiber being displaceably mounted in said holder and defining said radiation guide means.

11. A contact applicator arrangement for applying laser radiation to an object, the contact applicator arrangement comprising:

a holder having an outer surface fixed with respect to the applicator arrangement and defining a longitudinal axis;

said holder having an outlet formed in said surface for passing the radiation from said holder to the object;

radiation guide means mounted in said holder for guiding the radiation unfocused through said outlet to the object;

an element displaceably mounted in said holder so as to be movable along said axis in response to a contact pressure applied on said element, said element being movable to a first position wherein said element extends outwardly beyond said surface and to a second position rearward of said first position;

said first and second positions defining a displacement range of said element;

resilient biasing means for resiliently biasing said element in opposition to said contact pressure to define a pregiven force within said displacement range of said element;

laser radiation supply means for supplying radiation to said radiation guide means;

switching means for switching said radiation supply means on when said element is moved back to said first position and remaining on within said displacement range and for switching said radiation supply means off when said element reaches said second position and leaves said displacement range; and, said element being a tube displaceably mounted in said holder so as to be concentric to said axis and in surrounding relationship to said radiation guide means.

12. The contact applicator arrangement of claim 11, wherein said resilient biasing means applies a predetermined force to said element when said element reaches said first position.

13. The contact applicator arrangement of claim 11, wherein said switching means includes a first switch mounted in said holder for supplying an output signal when actuated and a first switch actuator mounted on said element to close said first switch when said element reaches said first position; and, said arrangement further including control means for controlling said radiation supply means to influence said radiation in response to said output signal.

14. The contact applicator arrangement of claim 11, further comprising adjusting means for adjusting the resilient force developed by said resilient biasing means to define a first limit force corresponding to said first position opposing said contact force and a second limit force corresponding to said second position opposing said contact force.

15. The contact applicator arrangement of claim 11, said radiation guide means being a light-wave conductor disposed in said tube.

16. The contact applicator arrangement of claim 15, said light-wave conductor being a fiber conductor.

* * * * *